(12) United States Patent
Verdier et al.

(10) Patent No.: US 8,356,524 B2
(45) Date of Patent: Jan. 22, 2013

(54) DEVICE FOR COLLECTING AND SEPARATING PARTICLES AND MICROORGANISMS PRESENT IN AMBIENT AIR

(75) Inventors: Amandine Verdier, Malakoff (FR); Emmanuelle Sorel, Rouvres (FR); Bruno Vallayer, Yvrac (FR); Denis Rebuffat, Anglet (FR)

(73) Assignee: Bertin Technologies, Montigny le Bretonneux (FR)

( * ) Notice: Subject to any disclaimer, the term of this patent is extended or adjusted under 35 U.S.C. 154(b) by 296 days.

(21) Appl. No.: 12/377,321

(22) PCT Filed: Aug. 30, 2007

(86) PCT No.: PCT/FR2007/001414
§ 371 (c)(1),
(2), (4) Date: Jun. 3, 2009

(87) PCT Pub. No.: WO2008/029014
PCT Pub. Date: Mar. 13, 2008

(65) Prior Publication Data
US 2010/0089173 A1 Apr. 15, 2010

(30) Foreign Application Priority Data
Sep. 4, 2006 (FR) ...................................... 06 07729

(51) Int. Cl.
*G01F 1/34* (2006.01)
(52) U.S. Cl. .................................................. 73/861.42
(58) Field of Classification Search ............... 73/863.21, 73/863.22
See application file for complete search history.

(56) References Cited

U.S. PATENT DOCUMENTS

| | | | | |
|---|---|---|---|---|
| 3,070,990 A * | 1/1963 | Krinov | ........................ | 73/23.31 |
| 4,133,202 A * | 1/1979 | Marple | ........................ | 73/28.06 |
| 4,137,751 A * | 2/1979 | Rhodes et al. | ................ | 73/28.04 |
| 4,530,250 A * | 7/1985 | Gay et al. | ................... | 73/863.12 |
| 4,725,294 A * | 2/1988 | Berger | ........................ | 73/863.22 |
| 5,412,975 A   | 5/1995 | Raabe et al. | | |
| 5,500,369 A * | 3/1996 | Kiplinger | ................... | 435/309.1 |
| 5,880,355 A * | 3/1999 | Park et al. | ................... | 73/28.01 |
| 5,882,529 A * | 3/1999 | Gupta | ........................... | 210/784 |
| 5,902,385 A   | 5/1999 | Willeke et al. | | |

(Continued)

FOREIGN PATENT DOCUMENTS
FR 2 855 831 12/2004
(Continued)

OTHER PUBLICATIONS

International Search Report for PCT/FR2007/001414 filed Aug. 30, 2007.

*Primary Examiner* — Hezron E Williams
*Assistant Examiner* — Mark A Shabman
(74) *Attorney, Agent, or Firm* — Alston & Bird LLP

(57) ABSTRACT

A device for collecting and separating particles and microorganisms present in ambient air, the device comprising suction means for sucking air into a removable centrifuging chamber (10) having an air inlet and outlet and forming a receptacle for transporting a liquid sample containing the collected particles and microorganisms, said enclosure (10) being selected from a set of enclosures having different diameters and suitable for enabling the same suction means to take samples at suction rates lying in the range about 100 liters per minute to about 2000 liters per minute.

16 Claims, 2 Drawing Sheets

U.S. PATENT DOCUMENTS

| | | | |
|---|---|---|---|
| 6,294,375 B1 * | 9/2001 | Chevalier | 435/287.1 |
| 6,550,347 B2 * | 4/2003 | Bradley | 73/863.21 |
| 6,692,553 B2 * | 2/2004 | Jordan et al. | 95/285 |
| 6,851,459 B2 * | 2/2005 | Squirrell et al. | 141/70 |
| 6,990,846 B2 * | 1/2006 | Sioutas | 73/28.05 |
| 7,125,437 B2 * | 10/2006 | Bryden et al. | 95/29 |
| 7,205,145 B2 * | 4/2007 | Ryan | 435/309.1 |
| 7,325,465 B2 * | 2/2008 | Solomon et al. | 73/863.22 |
| 7,452,394 B2 * | 11/2008 | Vallayer et al. | 55/337 |
| 7,785,408 B2 * | 8/2010 | Jordan et al. | 96/413 |
| 8,137,446 B2 * | 3/2012 | Plamondon et al. | 96/413 |
| 2003/0031573 A1 * | 2/2003 | Tearle | 417/534 |
| 2004/0173034 A1 | 9/2004 | Srebro | |
| 2006/0144025 A1 * | 7/2006 | Vallayer et al. | 55/428 |
| 2010/0089183 A1 * | 4/2010 | Solomon | 73/863.22 |
| 2010/0186524 A1 * | 7/2010 | Ariessohn et al. | 73/863.22 |

FOREIGN PATENT DOCUMENTS

FR 2855831 A1 * 12/2004

* cited by examiner

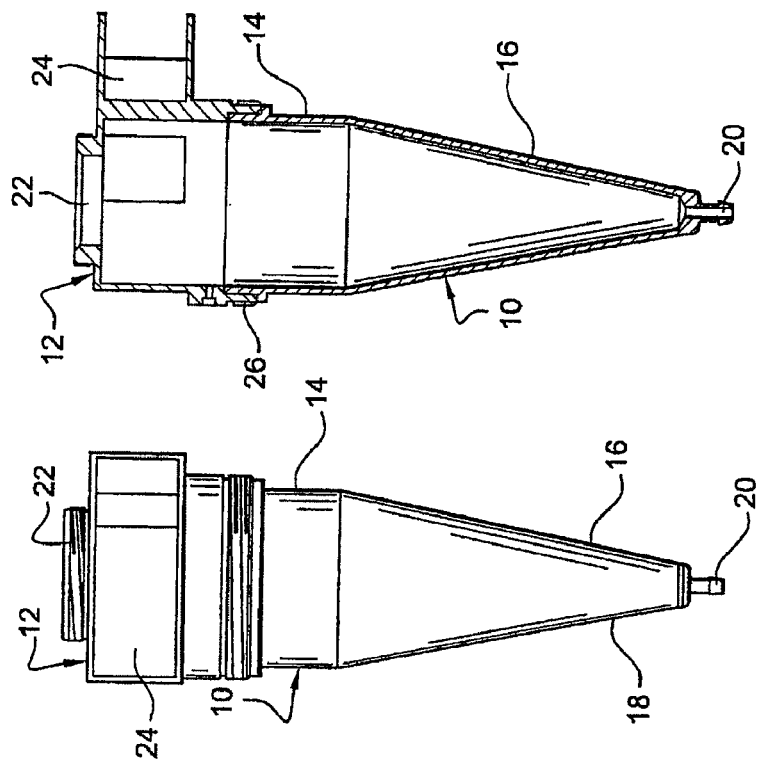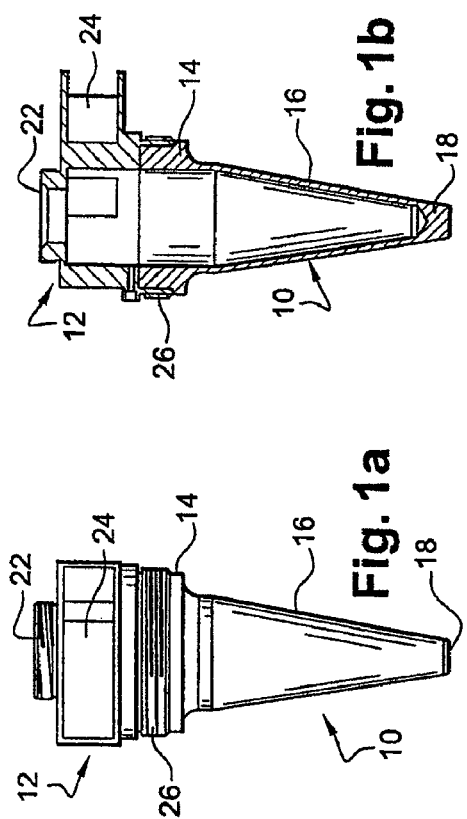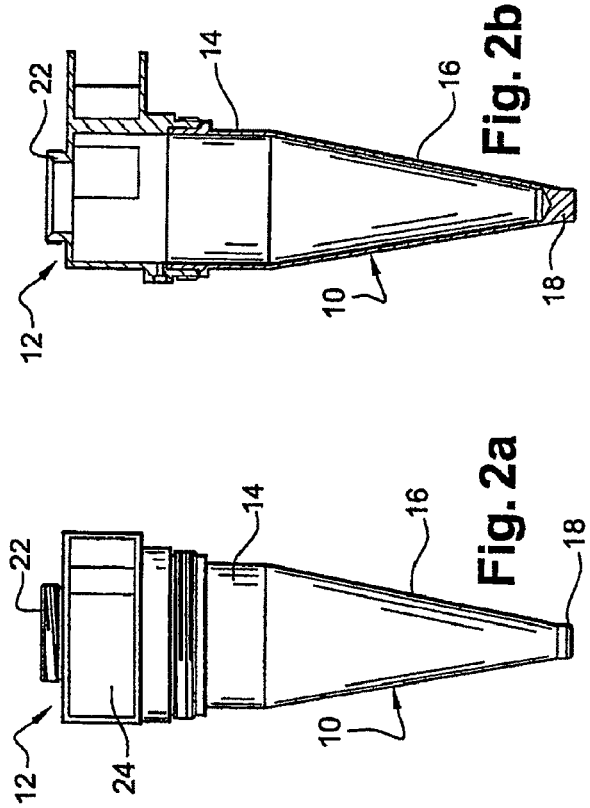

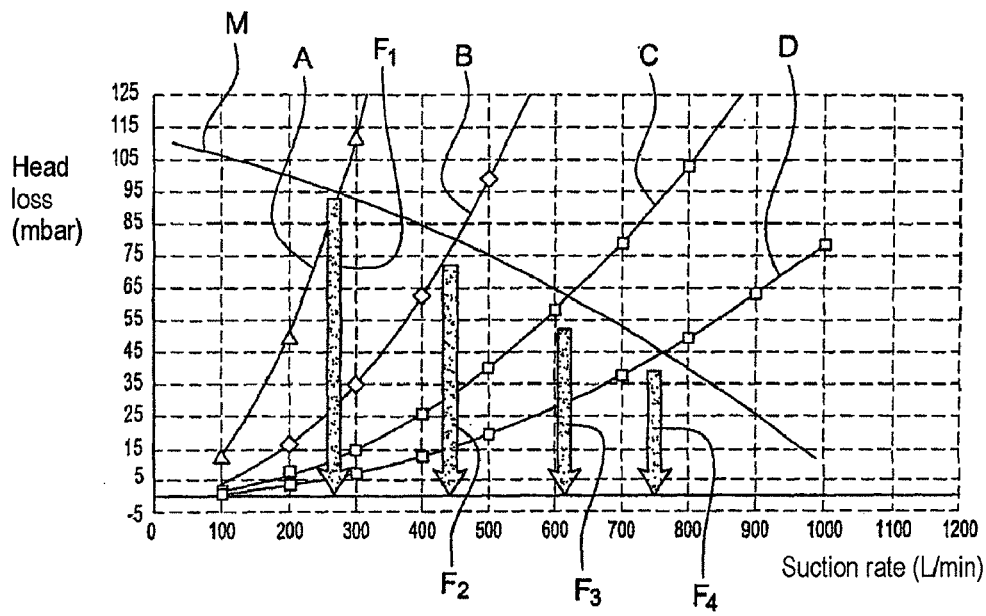
Fig. 4
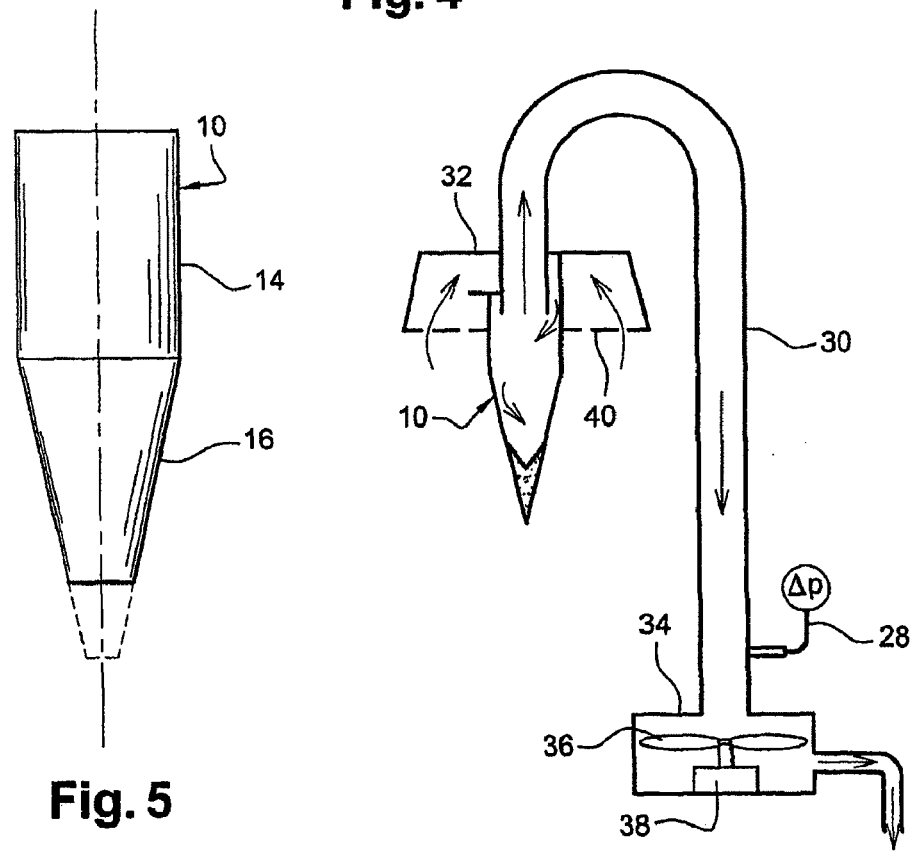
Fig. 5
Fig. 6

DEVICE FOR COLLECTING AND SEPARATING PARTICLES AND MICROORGANISMS PRESENT IN AMBIENT AIR

CROSS REFERENCE TO RELATED APPLICATIONS

This application is a national stage application filed under 35 U.S.C. 371 of International Application No. PCT/FR2007/001414, filed Aug. 30, 2007, which claims priority from French Application No. 06 07729, filed Sep. 4, 2006.

FIELD AND BACKGROUND OF THE INVENTION

The invention relates to a device for collecting and separating particles and microorganisms present in ambient air, for the purposes of identifying and counting such particles and microorganisms.

It is important to perform such identification and counting in numerous fields such as the pharmaceutical industry, the food industry, medical settings, hygiene services, veterinary services, site monitoring, etc., with the dimensions of the particles and microorganisms for collection lying in the range 0.5 micrometers (μm) to several tens of micrometers.

Document FR-A-2 855 831 discloses a device of this type that includes a removable centrifuging enclosure associated with air suction means, the enclosure having an air inlet and an air outlet and forming a container for transporting a liquid sample containing the collected particles and microorganisms.

It is desirable to be able to vary the sample-taking characteristics applied to particles and microorganisms as a function of the conditions in which such samples are taken, and for example:
  indoors or outdoors;
  for monitoring purposes that are continuous, or over a long duration, or in the event of an alarm;
  as a function of the characteristics of the microorganisms being collected.

In the event of an alarm, it is desirable in particular to take samples at a high rate of suction in order to obtain a result as quickly as possible. Conversely, when taking samples for monitoring purposes it is possible to use a lower rate over a longer period of time.

Similarly, relatively low suction rates are more suitable for preserving certain microorganisms.

At present there are no apparatuses in existence for collecting and separating particles and microorganisms present in ambient air and in which it is possible to cause the suction flow rate to vary over a large range under conditions that maintain the quality and the reliability of the samples taken.

SUMMARY OF THE INVENTION

A particular object of the invention is to satisfy this need.

To this end, the invention provides a device for collecting and separating particles and microorganisms present in ambient air, the device comprising suction means for sucking air into a removable centrifuging chamber having an air inlet and outlet and forming a receptacle for transporting a liquid sample containing the collected particles and microorganisms, the device being characterized in that said enclosure is selected from a set of enclosures having different diameters and suitable for enabling the same suction means to take samples at suction rates lying in the range about 100 liters per minute to about 2000 liters per minute.

By causing the diameter of the centrifuging enclosures to vary it is possible to cause the suction flow rates to vary over a large range while, ensuring the quality and the reliability of sample-taking.

In an embodiment of the invention, the diameters of the enclosures lie in the range about 20 mm to about 100 mm, for suction rates lying in the range about 100 liters per minute to 2000 liters per minute.

Each centrifuging enclosure comprises a cylindrical top portion connected to an air inlet and a conical bottom portion in which the sample-taking liquid accumulates. In order to conserve a quantity of sample-taking liquid that is more or less identical in each enclosure and that has the same separation efficiency regardless of the dimensions of the enclosure, it is advantageous for the bottom end of the conical portion of at least the largest enclosure to be truncated.

According to other characteristics of the invention:
  the enclosure is connected by a sample-taking pipe to a chamber containing the air suction means, said chamber possibly being disposed horizontally or vertically in its operating position;
  the device includes means for determining and/or monitoring the quantity of liquid in the enclosure and removable means for injecting liquid into the enclosure;
  the device includes means for measuring the flow rate of air sucked into the enclosure, said means comprising a pressure sensor mounted on the sample-taking pipe connecting the enclosure to the air suction means;
  the position where the pressure sensor is mounted on the sample-taking pipe is remote from the bend in the pipe at its end connected to the enclosure, and is remote from the suction means;
  the device includes a sample collection flask placed inside a cooled compartment, e.g. fitted with a Peltier effect thermoelectric element;
  the enclosure includes means at its bottom end for draining into a collection flask; and
  the enclosures are fitted with removable air inlet and outlet elements, the air inlet being of the unidirectional or omnidirectional type.

BRIEF DESCRIPTION OF THE DRAWINGS

The invention can be better understood and other characteristics, details, and advantages appear more clearly on reading the following description made by way of example with reference to the accompanying drawings, in which:

FIGS. 1a & 1b, 2a & 2b, and 3a & 3b are diagrammatic elevation and axial section views of respective sample-taking enclosures of different dimensions;

FIG. 4 is a graph showing the suction rate that can be achieved with a given motor for enclosures of different dimensions;

FIG. 5 is a diagram showing the general shape of an enclosure with its bottom end truncated; and FIG. 6 is a diagrammatic view of a device of the invention fitted with a pressure sensor for measuring the suction rate.

MORE DETAILED DESCRIPTION

In FIGS. 1a to 3b, the centrifuging enclosures 10 are shown in association with air inlet and outlet elements 12, and they are of different diameters, the enclosure 10 of FIGS. 1a and 1b having a diameter of 30 mm, the enclosure of FIGS. 2a and 2b having a diameter of 40 mm, and the enclosure of FIGS. 3a and 3b having a diameter of 50 mm.

The air inlet and outlet element 12 covers a top cylindrical portion 14 of the enclosure that is connected to a conical bottom portion 16 of section that decreases down to its bottom end 18 that may be closed as shown for the smaller enclosures of FIGS. 1a & 1b and 2a & 2b, or that may be provided with a tube and a valve 20 for delivering liquid as shown for the enclosure of FIGS. 3a and 3b, in order to drain the enclosure into a collection flask, the outlet tube 20 having opening and closing means such as a clamp, a solenoid valve, etc.

The air inlet and outlet element 12 fitted to each enclosure has a one-way inlet and comprises a transverse top wall formed with an axial endpiece 22 for connection to a J-shaped sample-taking pipe (shown diagrammatically in FIG. 6), and a cylindrical wall formed with a tangential air inlet 24 and an open bottom end that fits over the top cylindrical portion 14 of the enclosure 10 and that includes a cylindrical skirt 26 for releasably fastening to the top portion 14 of the enclosure 10. The air inlet and outlet element 12 may be fastened on the enclosure 10 in any appropriate manner, for example a quick screw-fastening, a bayonet fastening, resilient snap-fastening, etc.

The suction rates that can be achieved with these enclosures are shown in FIG. 4, where air suction rates are plotted along the abscissa and head loss is plotted up the ordinate, head loss occurring essentially in the air inlet 24 of the enclosure.

The suction rates that can be reached are a function of the suction means used and they may be determined from the characteristic curve M of the suction motor and from the air flow characteristics of the enclosures. In FIG. 4, curve A represents head loss as a function of suction flow rate for the enclosure 10 of FIGS. 1a and 1b, having a diameter of 30 mm, and arrow F1 indicates the rate that can be reached for this enclosure, i.e. about 280 liters per minute.

Similarly, curve B represents variation in head loss as a function of suction flow rate for the enclosure 10 of FIGS. 2a and 2b, having a diameter of 40 mm, arrow F2 indicating that the flow rate that can be reached with this enclosure is about 440 liters per minute. Curve C represents the variation in head loss as a function of suction flow rate for the enclosure 10 of FIGS. 3a and 3b having a diameter of about 50 mm, with arrow F3 corresponding to the flow rate that can be reached, which is about 610 liters per minute. Curve D represents the variation in head loss as a function of suction flow rate for an enclosure 10 having a diameter of 60 mm, with the corresponding reachable flow rate, indicated by arrow F4, being about 750 liters per minute.

In general, collection efficiency is the product of three factors: capture efficiency in suction; separation efficiency inside the enclosure; and recovery efficiency from the liquid contained in the enclosure.

Capture efficiency and separation efficiency depend relatively little on the size of the particles being captured or on variations in the suction flow rate. Liquid recovery efficiency depends on the quality with which the walls of the enclosure 10 are rinsed, on the volume of liquid contained in the enclosure, and on the speed of air flow in the enclosure. In particular, it is necessary for said speed to remain between a bottom limit and a top limit that correspond to volume flow rates of about 500 liters per minute and 700 liters per minute respectively for an enclosure having a diameter of 50 mm, and about 700 liters per minute to about 1000 liters per minute respectively for an enclosure having a diameter of 60 mm.

The volume of liquid contained in the enclosure and the air flow speed in the enclosure need to be sufficient to ensure that the walls of the enclosure are properly rinsed and they must avoid or at least limit entrainment of drops of liquid to the outside of the enclosure, since any liquid lost in this way contains particles and microorganisms that cannot be identified and counted.

To avoid the enclosures of the larger sizes, in particular those having a diameter of 50 mm or of 60 mm, containing too great a volume of liquid, it is possible to reduce the height of the conical bottom portion 16 of the enclosure, as represented diagrammatically in FIG. 5, by truncating it at its bottom end. This enables the volume of liquid contained in the enclosure 10 when taking a sample to be reduced by about 10 mL to 15 mL, and thus makes it possible to come closer to the volume of liquid that are contained in the enclosures 10 of smaller dimensions.

The volume of liquid used in the enclosure 10 of FIG. 5 thus becomes comparable to requirements, which may be 15 mL for example, thereby ensuring separation and recovery efficiency that remain substantially constant on changing enclosure.

It is also important to know accurately the quantity of air that has actually been sucked through by the end of sample-taking. Counting results are always relative to the volume of air sucked in. It is possible to measure flow rate internally by means of a low-cost pressure sensor 28 that may be connected to the sample-taking pipe 30 (FIG. 6) interconnecting the air inlet and outlet element 32 covering the enclosure 10 and a chamber 34 containing the air suction means, here constituted by a propeller 36 driven in rotation by an electric motor 38. In the example of FIG. 6, the air inlet and outlet element 32 has an omnidirectional air inlet, air being sucked in around the cylindrical top portion 14 of the enclosure 10 through a filter 40.

Tests have confirmed that there is a good correlation between the head loss measured by the sensor 28 and the flow rate of the sucked-in air. It is preferable for the sensor 28 to be connected to the sample-taking pipe 30 downstream from the bend in the pipe, with the distance between said bend and the connection point for the sensor 28 being, for example, about ten times the diameter of the sample-taking pipe 30, and it is also preferable for the connection point not to be too close to the inlet to the chamber 34, it being necessary for the sensor 28 to be spaced apart therefrom by a distance that corresponds to about three to four times the diameter of the sample-taking pipe 30.

By way of example, the negative pressure level with the connection is about 100 mbars, for a flow rate of 500 liters per minute with an enclosure 10 having a diameter of 40 mm. The sensor 28 used is a sensor that provides a differential pressure measurement, i.e. it measures the pressure drop relative to ambient atmospheric pressure. It is also possible to use an absolute pressure sensor that can also be used to determine ambient atmospheric pressure before beginning to take a sample.

The chamber 34 that contains the air suction means 36, 38 may include a compartment that is cooled, e.g. by means of a Peltier effect thermoelectric element, containing a flask for collecting the liquid sample contained in the bottom portion of the enclosure 10. This enables the liquid sample to be conserved at a predetermined low temperature, e.g. 8° C., when the liquid sample is not collected by an operator immediately after sample-taking. The cooled compartment is thermally insulated from the outside environment.

Provision can be made in the chamber 34 for means that inject liquid into the enclosure 10, either before the beginning of sample-taking, with the quantity of liquid then injected then corresponding to the volume of the liquid sample that is desired at the end of sample-taking, or else while sampling is taking place, in order to compensate for the liquid evaporating while taking samples over a relatively lengthy duration.

These liquid injection means may be removable and installed in the sample-taking pipe. For example they comprise a peristaltic pump connecting a flask of sampling liquid to a liquid inlet provided in the enclosure 10 or in the adjacent portion of the sample-taking pipe 30. Provision can also be made for means to measure or detect the level of liquid in the enclosure, such as soundwave means, a camera, etc., or to use charts recorded in a memory of the device and specifying the quantity of liquid to be injected as a function of the temperature and the humidity of the sample-taking site.

When taking a sample, it is also advantageous to open the outlet from the enclosure a few second before the end of sample-taking, while the sucked-in air is still swirling inside the enclosure, since that makes it easier for the sample to flow out from the enclosure.

The device of the invention is controlled by computer means of the personal computer (PC) type or of the personal digital assistant (PDA) type, serving to store data relating to the samples taken in memory (suction flow rates, sample-taking durations, start times, volumes of air actually sucked in, temperature and humidity, . . . ) and to perform a certain amount of automatic verification tests on the device and concerning proper operation thereof prior to taking a sample, such as, in particular:

reading a real time clock and displaying the current time;
verifying the ability to write and read in a backup memory;
reading the ambient temperature and humidity sensors;
reading the pressure sensor installed on the sample-taking pipe;
switching on and verifying the operation of the liquid injection pump;
switching on and verifying the operation of the solenoid valve;
displaying the result of the test performed for a few seconds; and
verifying and displaying the level of charge in the electric battery of the device.

Other information is also recorded prior to taking each sample or series of samples, such as the name of the operator, the serial number of the device, the sample-taking site, the activity at the sample-taking site, etc., in order to ensure that traceability for the samples taken.

The invention claimed is:

1. A device for collecting and separating particles and microorganisms present in ambient air, the device comprising:
an air inlet and outlet element;
a plurality of removable centrifuging enclosures, wherein each individual enclosure of said plurality of enclosures has a different diameter and is configured to be removably attached to the air inlet and outlet element, and wherein when attached to the air inlet and outlet element, each of the enclosures define a receptacle for transporting a liquid sample containing the collected particles and microorganisms,
suction means for sucking air into an individual enclosure attached to said air inlet and outlet element;
wherein said individual enclosure is selected from said plurality of enclosures such that a suction rate lying in the range about 100 liters per minute to about 2000 liters per minute is obtained with the same suction means.

2. The device according to claim 1, wherein the diameters of the enclosures lies in the range about 20 mm to about 100 mm.

3. The device according to claim 1, wherein the enclosures comprise a cylindrical top portion and a conical bottom portion, the bottom end of the conical portion of at least the largest enclosure being truncated so as to reduce the volume of sample-taking liquid contained in said enclosure.

4. The device according to claim 1, wherein the enclosure is connected by a J-shaped sample-taking pipe to a chamber containing the air suction means, said chamber possibly being disposed horizontally or vertically in its operating position.

5. The device according to claim 1, including means for determining and/or monitoring the quantity of liquid in the enclosure and removable means for injecting liquid into the enclosure.

6. The device according to claim 1, including means for measuring the flow rate of air sucked into the enclosure, said means comprising a pressure sensor mounted on the sample-taking pipe connecting the enclosure to the air suction means.

7. The device according to claim 6, wherein the position where the pressure sensor is mounted on the sample-taking pipe is remote from a bend in the pipe at its end connected to the enclosure, and is remote from the suction means.

8. The device according to claim 1, including a sample collection flask placed inside a cooled compartment fitted with a Peltier effect thermoelectric element.

9. The device according to claim 8, wherein the enclosure includes means at its bottom end for draining into a collection flask.

10. The device according to claim 1, wherein the enclosures are fitted with removable air inlet and outlet elements, the air inlet being of the unidirectional or omnidirectional type.

11. The device according to claim 1, including controlling computer means enabling data relating to the samples taken to be stored in memory and capable of performing automatic tests for verifying the device prior to taking samples.

12. The device of claim 1, wherein the air inlet and outlet element includes a cylindrical skirt configured to be removably attached to a top portion of an individual enclosure.

13. The device of claim 1, wherein the air inlet and outlet element includes a one-way inlet having a transverse top wall formed with an axial endpiece that is connected to a sample-taking pipe such that the air inlet and outlet element is in fluid communication with said suction means.

14. The device of claim 13, wherein the sample-taking pipe has a J-shape.

15. The device of claim 13, wherein the air inlet and outlet element includes a cylindrical wall having an air inlet that extends tangentially to said cylindrical wall.

16. A device for collecting and separating particles and microorganisms present in ambient air, the device comprising:
an air inlet and outlet element;
a plurality of removable centrifuging enclosures, wherein each individual enclosure of said plurality of enclosures has a different diameter and is configured to be removably attached to the air inlet and outlet element, and wherein when attached to the air inlet and outlet element, each of the enclosures define a receptacle for transporting a liquid sample containing the collected particles and microorganisms,
suction means for sucking air into an individual enclosure attached to said air inlet and outlet element; said air inlet and outlet element is configured to accept each individual enclosure so that each individual enclosure is interchangeably attachable to the air inlet and outlet element;

wherein said individual is selected from said plurality of enclosures such that a suction rate lying in the range about 100 liters per minute to about 2000 liters per minute is obtained with the same suction means.

* * * * *